(12) United States Patent
Hafner

(10) Patent No.: US 7,850,688 B2
(45) Date of Patent: *Dec. 14, 2010

(54) ELECTROSURGICAL INSTRUMENT

(75) Inventor: Dieter Hafner, Tubingen (DE)

(73) Assignee: ERBE Elektromedizin GmbH, Tübingen (DE)

( * ) Notice: Subject to any disclaimer, the term of this patent is extended or adjusted under 35 U.S.C. 154(b) by 815 days.

This patent is subject to a terminal disclaimer.

(21) Appl. No.: 11/573,280

(22) PCT Filed: Jul. 15, 2005

(86) PCT No.: PCT/EP2005/007738

§ 371 (c)(1),
(2), (4) Date: Feb. 6, 2007

(87) PCT Pub. No.: WO2006/018087

PCT Pub. Date: Feb. 23, 2006

(65) Prior Publication Data

US 2007/0233060 A1    Oct. 4, 2007

(30) Foreign Application Priority Data

Aug. 11, 2004 (DE) ............ 10 2004 039 052
Nov. 18, 2004 (DE) ............ 10 2004 055 671

(51) Int. Cl.
*A61B 18/18* (2006.01)
(52) U.S. Cl. ...................................... 606/51
(58) Field of Classification Search .......... 606/49–52, 606/205–207
See application file for complete search history.

(56) References Cited

U.S. PATENT DOCUMENTS

| | | | |
|---|---|---|---|
| 5,324,289 A * | 6/1994 | Eggers | 606/48 |
| 5,443,463 A | 8/1995 | Stern et al. | |
| 5,458,598 A | 10/1995 | Feinberg et al. | |
| 5,709,680 A * | 1/1998 | Yates et al. | 606/50 |
| 5,891,142 A | 4/1999 | Eggers et al. | |

(Continued)

FOREIGN PATENT DOCUMENTS

WO    9717033    5/1997

(Continued)

*Primary Examiner*—Thomas J Sweet
*Assistant Examiner*—Benjamin Lee
(74) *Attorney, Agent, or Firm*—Dickstein Shapiro LLP

(57) ABSTRACT

The invention relates to an electrosurgical instrument comprising two limbs that have an articulated connection and that can be actuated in the manner of a cutting or clamping tool. The instrument includes opposing electrode parts with coagulation surfaces on distal ends of its limbs for holding a vessel or tissue and for passing a current through said vessel or tissue to coagulate the latter and also current supply devices that supply the coagulation current from a high-frequency generator to the electrode parts. One of the coagulation surfaces is convex, at least in a first central section, and the opposing coagulation surface is concave, at least in a second central section. The radius of curvature of the concave coagulation surface is greater, at least in the second central section, than the radius of curvature of the convex coagulation surface in the first central section. The curvatures run along longitudinal axes of the distal ends in such a way that a vessel or tissue that is held between the distal ends runs perpendicularly to the longitudinal axes and is retained with a pressure that increases towards the first and second central sections.

15 Claims, 4 Drawing Sheets

U.S. PATENT DOCUMENTS

| | | |
|---|---|---|
| 6,267,761 B1 | 7/2001 | Ryan |
| 6,273,887 B1 | 8/2001 | Yamauchi et al. |
| 6,775,575 B2 * | 8/2004 | Bommannan et al. ....... 607/101 |
| 2001/0037109 A1 | 11/2001 | Yamauchi et al. |
| 2003/0109876 A1 | 6/2003 | Yamauchi |
| 2003/0171747 A1* | 9/2003 | Kanehira et al. ............. 606/45 |
| 2003/0181910 A1* | 9/2003 | Dycus et al. ................. 606/51 |
| 2004/0006340 A1 | 1/2004 | Latterell et al. |
| 2004/0049185 A1 | 3/2004 | Latterell et al. |
| 2004/0116979 A1 | 6/2004 | Truckai et al. |

FOREIGN PATENT DOCUMENTS

| | | |
|---|---|---|
| WO | WO 2004/032777 A1 | 4/2004 |

* cited by examiner

ELECTROSURGICAL INSTRUMENT

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The invention relates to an electrosurgical instrument comprising two limbs that have an articulated connection and that can be actuated in the manner of a cutting or clamping tool.

BACKGROUND OF THE INVENTION

Electrosurgical instruments have been used for many years in high-frequency surgery especially in order to coagulate biological tissue as well as to cut it. For coagulation a high-frequency current is passed through the tissue to be treated, so that it changes due to protein coagulation and dehydration. The tissue contracts in such a way that the vessels are closed and bleeding is staunched. After coagulation has taken effect the tissue can for example be separated by means of a mechanically operating cutting instrument.

Electrosurgical processes can be carried out in a monopolar as well as a bipolar way. With monopolar technology the electrosurgical instrument has only one current supply and the tissue to be treated (or the patient) must therefore be placed at the other potential. Bipolar instruments which are constructed with two separately isolated sections are gaining more and more in significance, however. The current path between the electrode parts can thus be calculated and does not run long distances through the body of the patient. The effect of for example pacemakers or other equipment which are connected to the patient during an operation is thus reduced.

Bipolar coagulation instruments comprise essentially two limbs that have an articulated connection at whose proximal ends handle devices are provided for handling the limbs. At the distal ends of the limbs are electrode parts with coagulation surfaces for gripping the tissue and for passing the coagulation current through the tissue. For this the HF current supplied by the HF generator is fed via the current supply devices to the electrode parts of the bipolar instrument.

The problem with conventional electrosurgical instruments, however, is that the tissue once gripped between electrode parts easily slides away or slips. This can lead to complications in particular when the operating area is difficult to see by the surgeon, for example with endoscopic procedures or with heavily bleeding sections of tissue and restoring a grip on the tissue is difficult.

Commercially available instruments are frequently manufactured with structured electro-parts that is to say with structured coagulation surfaces, so that the tissue is gripped securely between the coagulation surfaces of the electrode parts. The electrode parts comprise for example wave-shaped coagulation surfaces.

Structuring of coagulation surfaces is, however, involves many disadvantages. Even the manufacture of such coagulation surfaces is very expensive. In addition structuring promotes adherence of the tissue to the surfaces during the procedure, so that preparation for reuse is also very time-consuming. The complicated geometry also makes reconditioning of the coagulation surface difficult.

BRIEF SUMMARY OF THE INVENTION

It is an object of the invention to provide an electrosurgical instrument for coagulation of the above-mentioned type wherein tissue to be treated can be securely held between the electrode parts, and the instrument, in particular the coagulation surfaces, can easily be manufactured and prepared for reuse.

According to the invention there is provided an electrosurgical instrument which includes two limbs that have an articulated connection which can be operated as a cutting or clamping tool. The instrument also includes electrode parts with coagulation surfaces positioned opposite each other at distal ends of the limbs for gripping a vessel or tissue and for passing a coagulation current through the vessel or tissue for its coagulation, as well as current supply devices for supplying the coagulation current to the electrode parts from a HF generator. One of the coagulation surfaces is convex, at least in a first central section, whereby the radius of curvature of the concave coagulation surface is greater in at least the second central section than the radius of the curvature of the convex coagulation surface in the first central section and whereby the curvatures run along longitudinal axes of the distal ends in such a way that the vessel or tissue that is held between the distal ends and extends perpendicularly to the longitudinal axes is retained with increasing pressure towards the first and second central sections.

The terms "convex" and "concave" in this context are not just to be understood as a rounded arc. These terms both here and in the claims are intended to mean any kind of elevation or recess. Hence, the terms are intended to cover not only a surface which defines a rounded arc but also one in the form of a roof-like elevation or a V-shaped recess.

The basis of the invention is, that by creating coagulation surfaces with different curvatures, contact of the coagulation surfaces can, seen mathematically, only occur at their crests. This means that an area of maximal proximity is formed between the coagulation surfaces which extend symmetrically around the crests of the coagulation surfaces. Tissue is particularly strongly pressed together by the limbs brought together in this area as a result of the increased pressure compared to the remaining coagulation areas and is thus securely held between the electrode parts.

The problems in conventional electrosurgical instruments described above are advantageously overcome with the device according to the invention as the simple smooth geometry is easy to manufacture, inhibits the adherence of tissue during the procedure and can be easily prepared for reuse and reconditioning. In addition secure closure of the vessel or tissue is achieved as a result of the high clamping force in the area of high pressure.

In a first advantageous embodiment an insulating section is formed on at least one of the coagulation surfaces in the central section, so that direct electrical contact between the coagulation surfaces can be prevented. Due to the heat conducting properties of the insulating section coagulation of the tissue is also guaranteed at this section.

In a further preferred embodiment the insulating section is formed on the at least one coagulation surface in such a way that it projects above the same. In this case the insulating section does not just serve to insulate, but also to bend the tissue to be treated several times in order to achieve a better hold of the tissue between the distal ends of the electrosurgical instrument. Pressure is also increased still further at the insulating section.

The insulating section is preferably constructed from several part sections. This facilitates an especially secure hold of the tissue between the electrode parts because the tissue is bent several times at edges of the part sections of the insulating section.

In a further preferred embodiment the insulating section is formed on the at least one coagulation surface in such a way that it extends continuously along one crest of the coagulation surface and is essentially flush with it. This is possible because the insulating section at the respective central section is provided at the corresponding central section of the coagulation surface and so when bringing the limbs together the opposite coagulation surface is reached first and exclusively. It is advantageous that the insulating section in this embodiment is protected by being housed in the respective electrode part and is thus safe from wear.

One solution according to the invention provides for the insulating section being constructed from ceramic or diamond. Advantageously both ceramic and diamond have amongst other things a high corrosion and high wear resistance to mechanical stress.

A device preventing a short circuit between the electrode parts can also be provided at the limbs, for example. If for example a spacer has been arranged at them, the limbs cannot be brought together completely and a gap remains between the electrode parts.

It is advantageous that at least one electrode part comprises at least one open region for a cutting instrument to carry out a cutting procedure, so that at least one section of the open region is provided as a guide gap for the cutting instrument and this can be applied to the clamped tissue. The guide gap facilitates precise cutting of the tissue, especially with mechanically operated cutting tools.

With the construction of the electrode parts with coagulation surfaces having curvatures, as described above, the electrode parts form tensioning areas, so that the tissue is pulled, that is to say stretched by the tensioning areas in the direction of their end regions. The tissue under tension is then easier to cut by means of mechanically operated cutting instruments, as tissue fibres are aligned at right angles to the cutting direction and the tissue becomes thinner in the process. The force needed to completely cut a pretensioned tissue is considerably reduced and mechanical stress on the cutting instrument, in particular wear of the cutting section, is counteracted. The cutting process itself is also easier for the surgeon and the instrument is easier to handle. At the same time the tissue to be treated is securely held between the tensioning areas, particularly close to a cutting area, due to the varying radii of curvature of the electrode parts or of the tensioning areas.

It is preferred if the open region divides the respective electrode parts into at least two areas, so that the electrode parts have separation surfaces arranged parallel and opposite to each other. The open region is thus useable as a guide gap over its entire area. This type of guide gap facilitates an extremely precise cut, as the cutting instrument, especially a mechanically operated instrument, can be guided particularly precisely.

In a further preferred embodiment it is provided that the open region divides the respective electrode parts into at least two areas, so that the electrode parts have separation surfaces arranged opposite that taper relative to each other in the direction of the coagulation surfaces. As the separation surfaces of the respective electrode parts move towards the cutting area of the tissue there is a guaranteed continued precise control of the cutting instrument. The part of the open region that is expanded and facing away from the cutting area is particularly suitable for preparation for reuse, hence cleaning, of the instrument after the completed procedure or also for the later application of a coating to the separation surfaces with for example wear-proof ceramic, as the construction of the open region guarantees improved access.

The open regions are preferably provided at the opposite electrode parts whereby these are essentially aligned when the limbs are brought together. If only one open region has been formed at an electrode part this is especially suitable for cutting the tissue with for example a surgical knife, whereby the tissue rests completely on the opposite electrode part in a tensioned state. If open regions have been provided at both electrode parts surgical scissors can for example be used on the coagulated tissue and can separate the same easily. In order that a well-calculated cut can be carried out the open regions are preferably arranged in the central sections of the electrode parts.

In a preferred embodiment the cutting instrument is combined with the electrosurgical instrument. The cutting instrument is for example situated within one of the limbs and can be brought into a cutting position, if so required. A change of instruments is thus avoidable, so that the course of an operation does not have to be interrupted. With the cutting instrument integrated in the coagulation instrument both electrode parts are preferably constructed with the open region, so that the cutting instrument can reach the tissue unhindered.

If the cutting instrument is not constructed so that it is integrated with the electrosurgical instrument the guide gap has then to be arranged in such a way that a cutting instrument being introduced from the outside can be placed with sufficient accuracy on the pretensioned tissue.

It is provided in one advantageous embodiment that the cutting instrument is mechanically and/or electrically operated. In this way a blade constructed on a shaft can for example be provided on the electrosurgical instrument which is housed in the limb during coagulation and is applied to the tissue for the cutting procedure. Positioning of the blade or another cutting instrument, as well as a forward movement, can occur automatically or can be carried out by the surgeon mechanically.

A solution according to the invention provides for a construction of the cutting instrument for cutting by means of HF-current and a connection to a control unit, so that the cutting current can be supplied depending on the phase of the operation. The surgeon can control the cutting process so that it runs automatically and is optimized.

A solution according to the invention provides for surface profile which supports a tensioning effect on the tissue brought about by the curvature being formed at the one electrode part and/or at the opposite electrode part. The profile is preferably formed at the end regions of the respective electrode parts and additionally moves the tissue in a direction of pull defined by the electrode parts or prevents a backward move of the tissue against this direction of pull.

The surface profile supporting the tensioning effect is preferably constructed as a saw tooth profile. Teeth of the profile can for example be arranged in such a way that during bringing the together of the limbs they continue to grip the tissue and transport it in the direction of pull. This increases the tension in the tissue considerably. Care must, however, be taken that an injury of the tissue caused by the profile is avoided, so that the teeth are preferably designed to have rounded-off nodules.

The profile is preferably constructed in such a way that the tissue is held by the profile in its tensioned position when the limbs are opened slightly. The profile acts therefore as an arrangement of barbs.

In a further preferred embodiment the insulating section or every insulating section is formed as the surface which supports the tensioning effect. A short circuit is thus prevented from occurring between the electrode parts in the simplest way, as well as the tensioning of the tissue being increased.

Electrosurgical instruments of this kind can for example be constructed for use on an open body cavity. The principle of the electrode parts having a curvature can also be employed in instruments for endoscopy. The electrode parts attached to the limbs, and if required, the cutting instrument are then for example operated via a handle attached to a shaft or a control unit is provided, so that actuation of the electrode parts and/or the cutting instrument is controlled by it. The electrosurgical instrument is thus preferably constructed as a laparoscopic instrument.

The invention will now be described by way of example with reference to the accompanying drawings.

DETAILED DESCRIPTION OF THE INVENTION

The same reference numbers will be used for the same parts and parts with the same functions.

Figure 1:
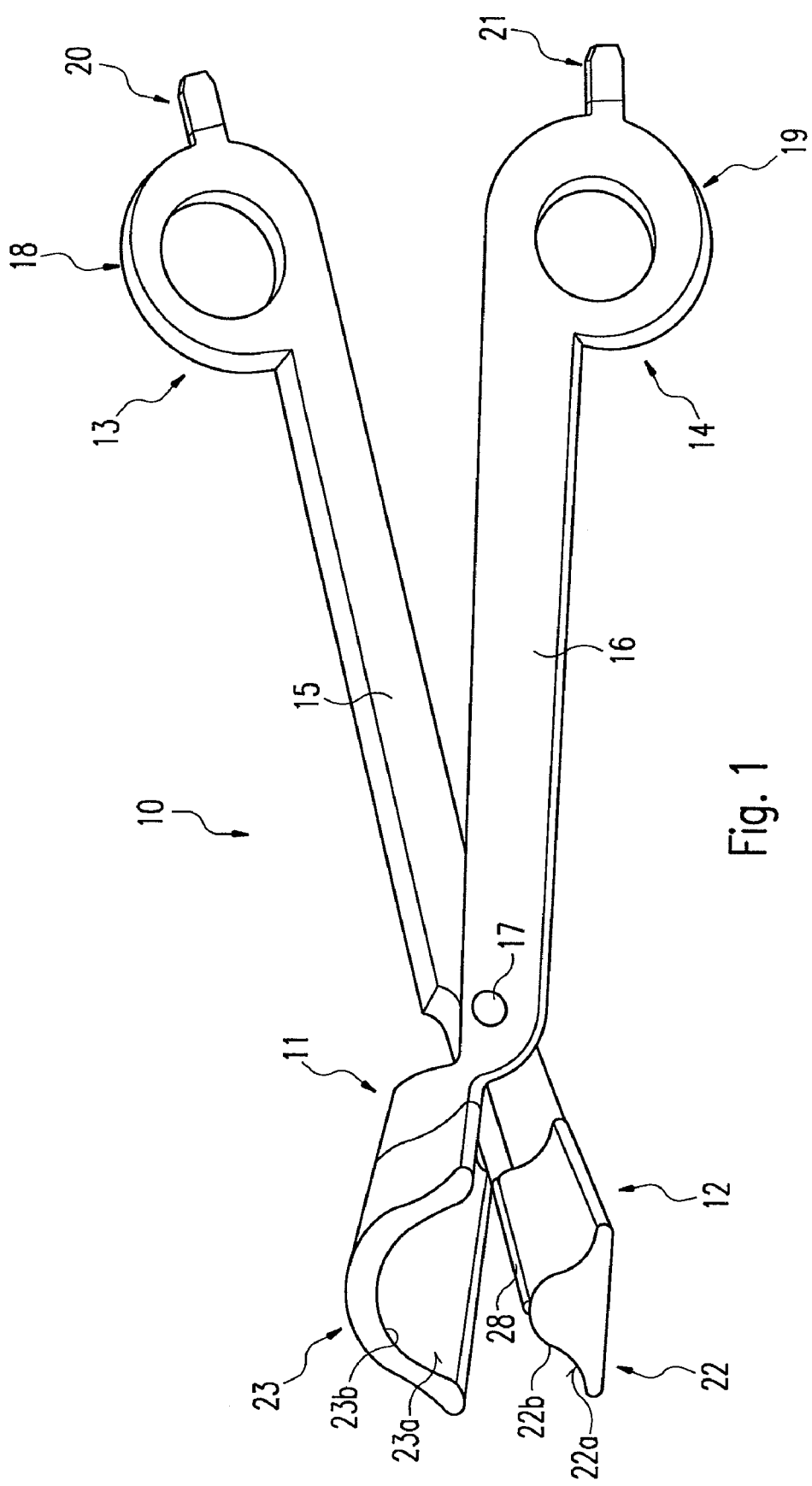
FIG. 1 is a perspective view of a first embodiment of electrosurgical instrument with an electrode arrangement according to the invention.
Figure 3:
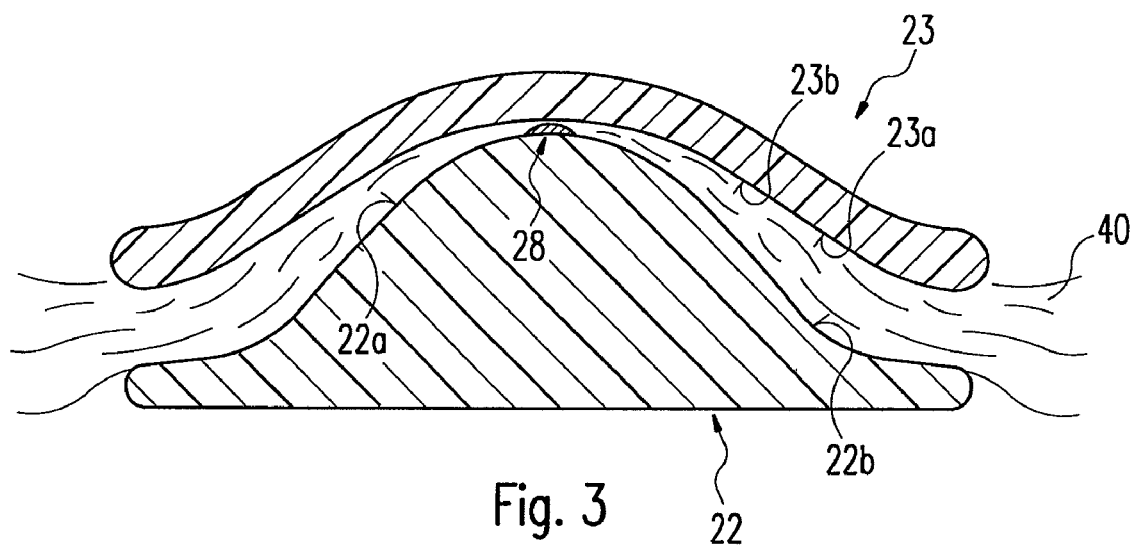
FIG. 3 is a schematic sectional view of the electrode arrangement as viewed from the front of the embodiment shown in FIG. 1.

FIG. 1 shows a perspective drawing of an electrosurgical instrument 10 with an electrode layout according to the invention in a first preferred embodiment. FIG. 3 shows the electrode layout in a front section view of the first preferred embodiment. The instrument 10 is constructed for a procedure on an open body cavity. Two limbs of the electrosurgical instrument 10 are identified in the Figure by the reference numerals 15 and 16. The two limbs 15, 16 are connected to each other via a spindle and can swivel around the same. They comprise distal ends 11, 12 fitted with electrode parts 22, 23, whereby the electrode parts 22, 23 are positioned opposite each other. A vessel or tissue 40 can for example be gripped by the electrode parts 22, 23 having coagulation surfaces 22a, 23a and be coagulated by means of a HF current being passed through it. Moreover, handles 18, 19 are provided which connect to the respective proximal ends 13, 14 of the limbs 15, 16. The proximal ends 13, 14 of the limbs 15, 16 each end in a current connection element or a current supply device 20, 21 for the connection of the electrosurgical instrument 10 to a HF generator (not depicted), which generates HF voltage, so that the HF current can for example be passed through the electric cables (not shown) running through the instrument 10 to the electrode parts 22, 23.

The electrosurgical instrument 10 is constructed in such a way that one electrode part 23 is moved over the other electrode part 22, that is to say it covers it, when the limbs 15, 16 are brought together. As can be seen from the Figure the electrode parts 22, 23 are curved. One electrode part 22 has a convex curvature 22b in a first central section and electrode part 23 positioned opposite the convex electrode part has a concave curvature 23b in a second central section. The radius of curvature of the coagulation surface with the concave curvature is larger than a radius of curvature of the coagulation surface with a convex curvature. The curvatures 22b, 23b run along longitudinal axes of the distal ends 11, 12 in such a way that the vessel or tissue 40 that is held between the distal ends 11, 12 and extends perpendicularly to the longitudinal axes is retained with an increasing pressure from the first and second central section.

Based on the curvature design of the coagulation surfaces 22a, 23a or the electrode parts 22, 23 contact between the coagulation surfaces 22a, 23a can, seen mathematically, occur only at their crests. This means that between coagulation surfaces 22a, 23a an area of maximal proximity is formed which extends symmetrically around the crests of the coagulation surfaces 22a, 23a. The tissue 40 is particularly strongly pressed together by the limbs 15, 16 being brought together in this area as a result of the increased pressure compared to the remaining coagulation areas and is thus safely held between the electrode parts 22, 23.

The simple, smooth geometry of the coagulation surfaces 22a, 23a is easy and cheap to manufacture. This also inhibits the adherence of tissue remains during the operation, so that the surfaces are easier to clean when preparing for reuse. Any re-working of the coagulation surfaces 22a, 23a can therefore be carried out easily based on this simple geometry. In addition safe closure of a vessel or tissue 40 is achieved as a result of the high clamping force in the area of high pressure.

On the crest of the electrode part 22 having a convex curvature a continuous insulating section 28 is arranged on the coagulation surface 22a. The insulating section 28 reliably prevents complete contact of the coagulation surfaces 22a, 23a and thus prevents a short circuit. In addition the insulating section 28 increases the force on the tissue 40. As the tissue 40 is additionally bent at the insulating section 28 a further improvement with respect to holding the tissue 40 can be achieved.

Alternatively it would be possible to construct the insulating section at the coagulation surface 22a in such a way that it also extends continuously along the crest of the coagulation surface 22a and is essentially flush with the same. The insulating section is then set into the coagulation surface 22a. This is possible because the insulating section would be provided for the first central section of the coagulation surface 22a and would thus reach the opposite coagulation surface 23a first and exclusively when the limbs 15, 16 are brought together. It would be advantageous if the insulating section in this embodiment is protected by being housed in the respective electrode part 22 and be thus safe from wear.

The insulating section 28 is preferably constructed from ceramic or diamond. Both materials show amongst other things a high resistance to corrosion and wear under mechanical stress.

Figure 2:
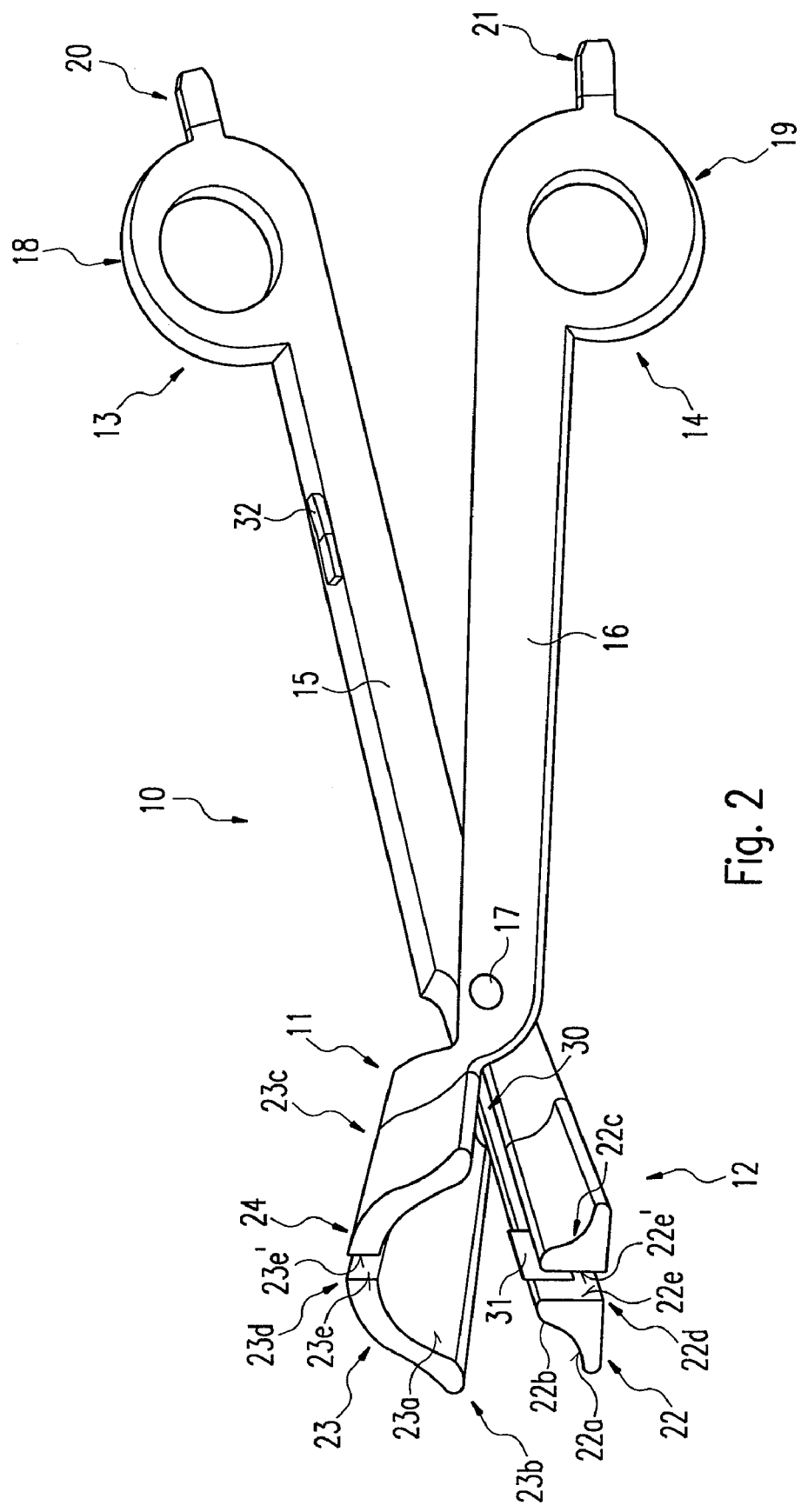
FIG. 2 is a perspective view of a second embodiment of electrosurgical instrument with an electrode arrangement according to the invention.

FIG. 2 shows a perspective drawing of an electrosurgical instrument 10 with an electrode layout according to the invention in a second preferred embodiment. The instrument is in principle similar to the one shown in FIG. 1, but comprises separate electrode parts 22, 23.

The electrode parts 22, 23 comprise open regions 22d, 23d which form a guide gap 24 for a cutting instrument 30. The cutting instrument 30 can therefore be placed on clamped tissue for a cutting procedure. As a result of the electrode parts 22, 23 having a curvature the tissue is pulled in the direction of the ends of the electrode parts 22, 23, that is to say it is stretched in the direction of pull. The electrode parts 22, 23 thus form tensioning areas 22c, 23c. The tissue under tension is then easier to cut, as tissue fibres are aligned at right angles to the cutting direction and the tissue becomes thinner in the process. When the limbs 15, 16 are brought together the tissue between the limbs 15, 16 is fixed in a tensioned state. The electrode parts 22, 23 in this embodiment are essentially formed wholly as tensioning areas 22c, 23c. Alternatively it is also possible that only sections of the electrode parts 22, 23 form tensioning areas.

The guide gap 24 facilitates precise cutting of the tissue, because the cutting instrument 30 is guided along the guide gap 24. This is particularly advantageous when the cutting instrument is operated mechanically. The tensioning areas 22c, 23c at the same time prevent tissue ingress into the guide gap 24, as the tissue is pulled out and away from it due to the tension.

As both tensioning areas 22c, 23c comprise open regions 22d, 23d they are arranged aligned to each other. Precise control of the cutting instrument 30 can only be guaranteed in this way.

As shown in this embodiment the open regions 22d, 23d divide the respective electrode parts 22, 23 into at least two areas, so that the electrode parts 22, 23 have respective separate surfaces 22e, 22e' or 23e, 23e' arranged opposite and parallel to each other. The open regions 22d, 23d can thus be used over their entire length as guide gap 24. This type of guide gap 24 facilitates an extremely precise cut, as the cutting instrument 30 can be guided especially precisely in particular if it is mechanically operated.

Alternatively it would be possible to construct only one open region at an electrode part, so that the tissue can for example be cut with a surgical knife. The tissue then rests completely on the opposite electrode part in a tensioned state.

The cutting instrument 30 comprises a blade 31 on a shaft and is housed during a coagulation phase within the limb 15. For the cutting process the cutting instrument 30 can be positioned on the already coagulated tissue and for cutting the tissue it can be moved at a defined feed speed. This occurs in this embodiment for example by means of a control unit (not shown) which controls the cutting instrument 30 that is activated by a finger switch 32. As the cutting instrument 30 is integrated in the electrosurgical instrument 10 a change of instruments and thus an interruption of an operating process are avoidable.

Alternatively, it also possible for the surgeon to actuate the cutting instrument mechanically. The surgeon can push the blade 31 when required through the limb 15 up to and through the tissue.

If no device for cutting tissue is provided on the electrosurgical instrument the guide gap 24 has then to be arranged in such a way that a cutting instrument introduced from the outside, for example surgical scissors, can be placed with sufficient accuracy on the pretensioned tissue.

In practical applications a spacer (not shown) or similar device maintaining a gap between the electrode parts 22, 23 is constructed on the electrosurgical instrument 10, so that direct contact of the coagulation surfaces 22a, 23a of the electrode parts 22, 23 can be prevented and thus also a short circuit. The spacer can for example be formed at one of the limbs 15, 16.

The electrosurgical instruments 10 shown in FIG. 1 and FIG. 2 are, as already mentioned, constructed for use on an open body cavity. The principle of the electrode parts 22, 23 formed with the tensioning areas 22c, 23c and the different radii of curvature can also be employed in endoscopes. The electrode parts attached to the limbs and if required the cutting instrument are then for example actuated via a handle attached to a shaft or a control unit is provided, so that actuation of the electrode parts and/or the cutting instrument is controlled by it.

Figure 4:
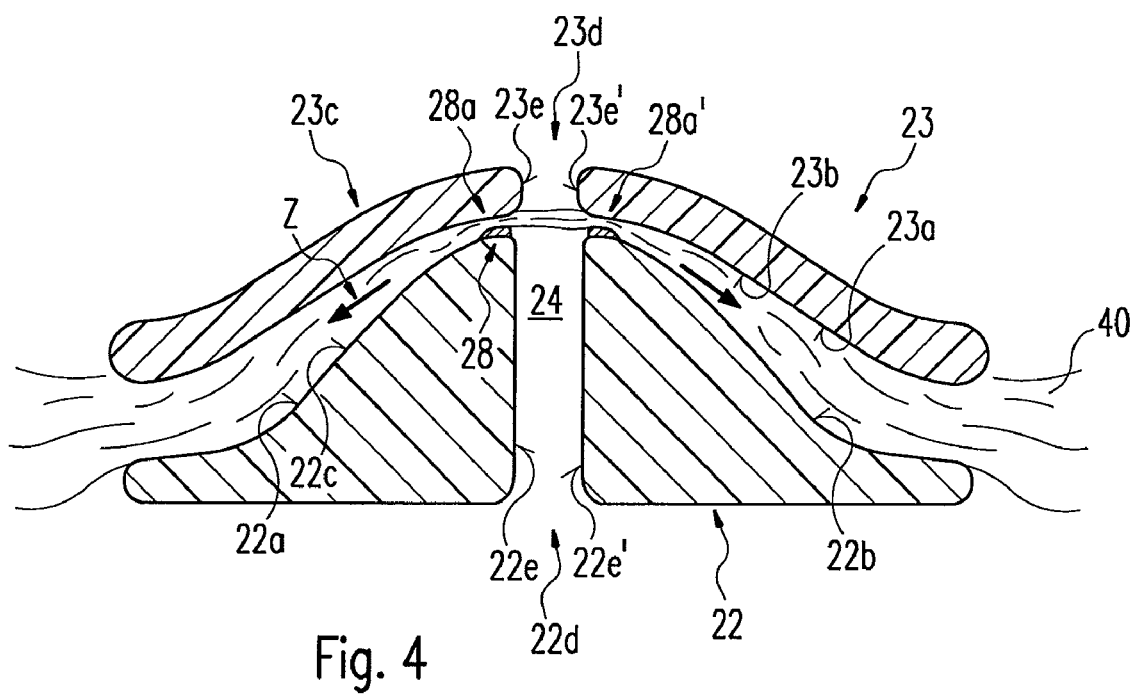
FIG. 4 is a schematic sectional view of an electrode arrangement as viewed from the front of a view third embodiment of electrosurgical instrument.
Figure 5:
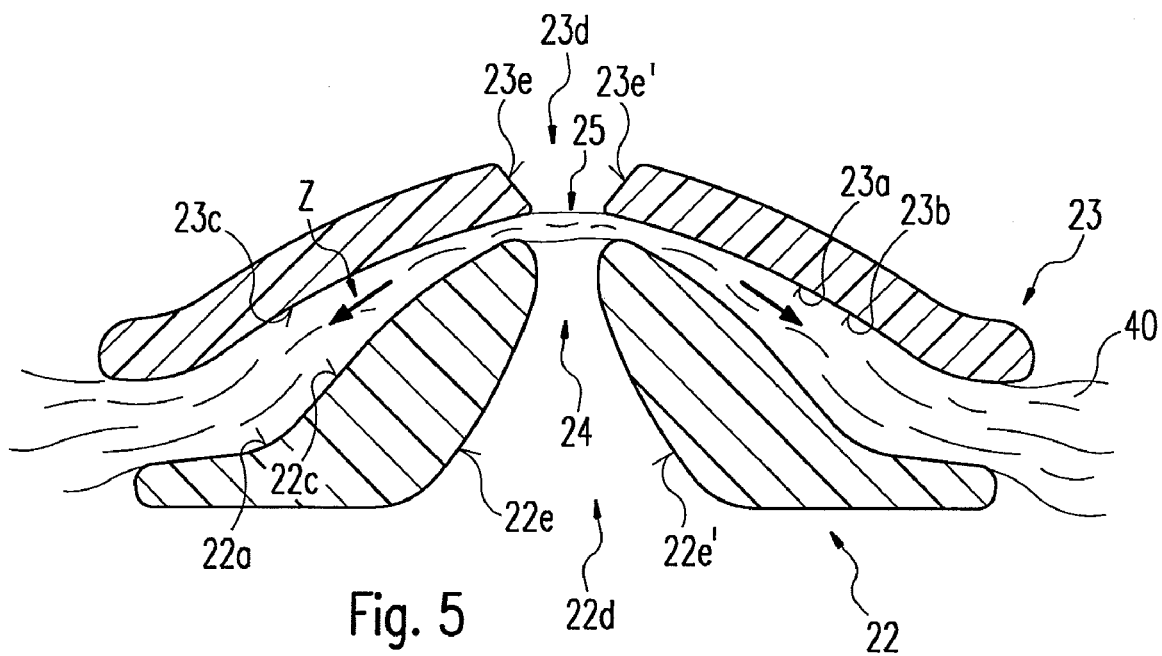
FIG. 5 is a schematic sectional view of an electrode arrangement as viewed from the front of a view fourth embodiment of electrosurgical instrument.
Figure 6:
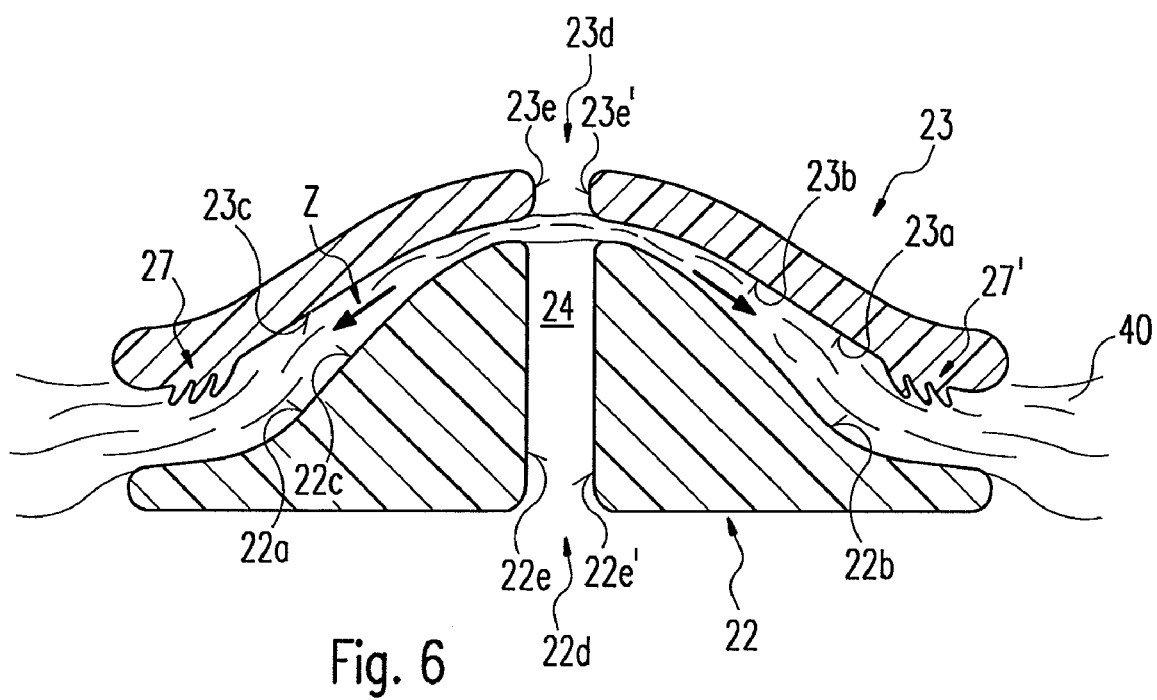
FIG. 6 is a schematic sectional view of an electrode arrangement as viewed from the front of a view fifth embodiment of electrosurgical instrument.

FIGS. 4 to 6 shows respectively a greatly enlarged front sectional view of an electrode layout in a third, fourth and fifth embodiment. The electrode parts 22, 23 correspond essentially to the embodiment of that shown in FIG. 2. They also comprise open regions 22d, 23d serving as guide gap 24 for a cutting instrument, as described in FIG. 2. In these embodiments, as already described in FIG. 1, the electrode part 22 has a convex curvature in a first central section while the electrode part 23 positioned opposite has a concave curvature in a second central section. The radius of curvature of the coagulation surface with the concave curvature is larger than the radius of curvature of the coagulation surface with a convex curvature. The curvatures 22b, 23b run along longitudinal axes of the distal ends in such a way that the vessel or tissue 40 that is held between the distal ends and extends perpendicularly to the longitudinal axes is retained with a pressure that increases towards the first and second central sections. As a result of the curvatures 22b, 23b the electrode parts 22, 23 in this embodiment are constructed as tensioning areas 22c, 23c. As a result of the tensioning areas 22c, 23c the tissue 40 is stretched in a direction of pull Z towards the ends of the electrode parts 22, 23. The fibres of the tissue 40 then align themselves at right angles to the cutting direction, so that the tissue is easier to cut while at the same time it is securely fixed in the electrode parts 22, 23 with different curvatures.

FIG. 4 shows the electrode layout according to the third preferred embodiment. This differs essentially from the electrode layout shown in FIG. 2 only in that a protruding insulating section 28, formed from two part sections 28a, 28a', is provided directly adjacent to an open region 22d at the convex electrode part 22 which is divided by the open region 22d into two areas. The part sections 28a, 28a' of the insulating section 28 extend preferably parallel to a crest of the electrode part. A short circuit between the electrode parts 22, 23 is thus prevented when they are brought together. The part sections 28a, 28a' of the insulating section 28 support the tensioning effect of the tension area 22 on the one hand and facilitate bending of the clamped tissue 40 on the other. Reliable holding of it between the electrode parts 22, 23 is thus guaranteed.

FIG. 5 also shows an electrode layout according to a fourth preferred embodiment. The electrode parts 22, 23 can also be seen here in a front sectional view. The electrode parts 22, 23 comprise open regions which differ from those shown in FIG. 2. The open regions 22d, 23d divide the respective electrode parts 22, 23 into two areas in such a way that the electrode parts 22, 23 have respective separation surfaces 22e, 22e' or 23e, 23e' arranged opposite that taper relative to each other in the direction of the coagulation surface 22a, 23a. As the separation surfaces 22e, 22e', 23e, 23e' of the respective electrode parts 22, 23 move towards a cutting area 25, continued precise control of the cutting instrument is guaranteed. The part of the open regions 22d, 23d facing away from the cutting area 25 is particularly suitable for preparation for reuse and also for cleaning of the instrument after the completed procedure or also for the later application of a coating to the separation surfaces 22e, 22e', 23e, 23e' with for example wear-resistant ceramic, as the construction of the open region 22d, 23d guarantees improved access.

The electrode layout shown in FIG. 6 is described essentially in FIG. 2. The electrode part 23 having a concave curvature 23b comprises a saw tooth profile 27, 27' at the ends. The teeth can for example be arranged in such a way that they continue to grip the tissue and transport it in the direction of pull Z while the limbs are brought together. This increases the tension in the tissue 40 considerably. Care must, however, be taken that injuries to the tissue 40 caused by the profile 27, 27' are avoided, so the teeth are preferably constructed as nodules.

The nodules are preferably laid out in such a way that the tissue 40 is held by the profile 27, 27' in its tensioned position when the limbs are opened slightly. The profile 27, 27' acts therefore as an arrangement of barbs.

In FIG. 6, an insulating section 28 (as shown in FIG. 4) can advantageously be formed between the electrode parts as a surface profile supporting the tensioning effect of the tensioning areas. Short circuits are thus prevented from occurring between the electrode parts in the simplest way and the tensioning of the tissue is also increased.

List of Reference Numerals
10 Electrosurgical instrument
11 Distal end
12 Distal end
13 Proximal end
14 Proximal end
15 Limb
16 Limb
17 Spindle
18 Handle
19 Handle
20 Current connection element, current supply device
21 Current connection element, current supply device
22 Electrode part
22a Coagulation surface
22b Convex curvature
22c Tensioning area
22d Open region
22e, 22e' Separation surface
23 Electrode part
23a Coagulation surface
23b Concave curvature
23c Tensioning area
23d Open region
23e, 23e' Separation surface
24 Guide gap
25 Cutting area
27, 27' Profile
28 Insulating section
28a, 28a' Part section of the insulating section
30 Cutting instrument
31 Blade
32 Finger switch
40 Tissue, vessel
Z Direction of pull

The invention claimed is:

1. An electrosurgical instrument including two limbs articulated in the manner of connection which can be actuated corresponding to a cutting or a clamping tool, electrode parts positioned opposite each other at distal ends of the limbs for gripping tissue and adapted to pass a coagulation current through said tissue for its coagulation, current supply devices adapted to supply said coagulation current to said electrode parts from a HF generator wherein opposing coagulation surfaces respectively defined by said electrode parts, one of said coagulation surfaces being convex at least in a first central section and said opposing coagulation surface being concave at least in a second central section, and the radius of curvature of the concave coagulation surface being greater in at least the second central section than the radius of curvature of the convex coagulation surface in the first central section, said curvatures running along longitudinal axes of said distal ends of the limbs such that tissue gripped between said distal ends extends perpendicularly to said longitudinal axes and is retained by a pressure that increases in directions towards said first and said second central sections, wherein the electrode parts form tensioning areas, so that the tissue is stretched in a direction of pull Z towards the ends of the electrode parts and wherein at least one electrode part defines at least one open region into which a cutting instrument is insertable for carrying out a cutting procedure on said gripped tissue, at least one section of said open region being adapted as a guide for said cutting instrument,
wherein
each electrode part defines at least one open region that divides the respective electrode part into at least two areas, whereby said electrode parts define respective separation surfaces arranged opposite and parallel to each other.

2. The electrosurgical instrument according to claim 1, wherein an insulating section is provided in the central section of at least one of said coagulation surfaces to prevent direct electrical contact between said coagulation surfaces.

3. The electrosurgical instrument according to claim 2, wherein said insulating section protrudes from said at least one coagulation surface.

4. The electrosurgical instrument according to claim 2 wherein said insulating section is formed from several part sections.

5. The electrosurgical instrument according to claim 2, wherein said insulating section extends continuously along a crest of said at least one coagulation surface and is substantially flush with said coagulation surface.

6. The electrosurgical instrument according to claim 2, wherein said insulating section is constructed from a ceramic or diamond.

7. The electrosurgical instrument according to claim 2, wherein at least one of said insulating sections defines a surface profile that produces a tensioning effect on the tissue.

8. The electrosurgical instrument according to claim 1, wherein opposite electrode parts each define at least one open region that is substantially aligned when said limbs are brought together.

9. The electrosurgical instrument according to claim 1, comprising a cutting instrument integrally constructed therewith.

10. The electrosurgical instrument according to claim 9, wherein said cutting instrument is actuated by at least one of a mechanical or an electrical means.

11. The electrosurgical instrument according to claim 10, wherein said cutting instrument is adapted to cut by means of an HF current supplied via a control unit whereby said current is supplied depending on the operating phases.

12. The electrosurgical instrument according to claim 1 wherein at least one of said electrode part defines a surface profile that produces a tensioning effect on the tissue.

13. The electrosurgical instrument according to claim 12, wherein said surface profile is a saw tooth profile.

14. The electrosurgical instrument according to claim 1, that is constructed as a laparoscopic instrument.

15. An electrosurgical instrument including
two limbs articulated in the manner of connection which can be actuated corresponding, to a cutting or a clamping tool,
electrode parts positioned opposite each other at distal ends of the limbs for gripping tissue and adapted to pass a coagulation current through said tissue for its coagulation,
current supply devices adapted to supply said coagulation current to said electrode parts from a HF generator
wherein opposing coagulation surfaces respectively defined by said electrode parts. one of said coagulation surfaces being convex at least in a first central section and said opposing coagulation surface being concave at least in a second central section, and the radius of curvature of the concave coagulation surface being greater in at least the second central section than the radius of curvature of the convex coagulation surface in the first central section, said curvatures running along longitudinal axes of said distal ends of the limbs such that tissue gripped between said distal ends extends perpendicularly to said longitudinal axes and is retained by a pressure that increases in directions towards said first and said second central sections,
wherein
the electrode parts form tensioning areas, so that the tissue is stretched in. a direction of pull Z towards the ends of the electrode parts and wherein at least one electrode part defines at least one open region into which a cutting instrument is insertable for carrying out a cutting procedure on said gripped tissue, at least one section of said open region being adapted as a guide for said cutting instrument, and
wherein
each electrode part defines at least one open region that divides the respective electrode part into at least two areas, whereby said electrode parts define respective separation surfaces arranged opposite to each other and that taper towards each other in the direction of said coagulation surfaces.

\* \* \* \* \*